United States Patent [19]
Sultze et al.

[11] Patent Number: 5,252,275
[45] Date of Patent: Oct. 12, 1993

[54] METHOD OF DENSIFYING CROSSLINKED FIBERS

[75] Inventors: Rolland F. Sultze, Everett; Fred B. Howard, Gig Harbor; Peter A. Graef, Tacoma, all of Wash.

[73] Assignee: Weyerhaeuser Company, Tacoma, Wash.

[21] Appl. No.: 665,761

[22] Filed: Mar. 7, 1991

[51] Int. Cl.⁵ .............................................. B29C 59/00
[52] U.S. Cl. .................................... 264/119; 264/126; 428/280
[58] Field of Search ............... 264/175, 257, 319, 324, 264/119, 126, 109; 428/280; 8/115.51, 116.1, 185

[56] References Cited

U.S. PATENT DOCUMENTS

| | | | |
|---|---|---|---|
| 3,440,135 | 4/1969 | Chung | 162/157 |
| 3,657,619 | 3/1972 | Mack et al. | 162/206 |
| 3,658,613 | 4/1972 | Steiger | 156/153 |
| 3,819,470 | 6/1974 | Shaw et al. | 162/157 |
| 4,287,823 | 8/1981 | Thompson | 100/129 |
| 4,453,461 | 6/1984 | Fleissner | 100/255 |
| 4,610,678 | 9/1986 | Weisman et al. | 604/368 |
| 4,822,453 | 4/1989 | Dean et al. | 162/157 |
| 4,853,086 | 8/1989 | Graef | 162/157 |
| 4,889,595 | 12/1989 | Herron et al. | 162/157 |
| 4,935,022 | 6/1990 | Lash et al. | 604/368 |
| 4,942,719 | 7/1990 | Fleissner | 53/436 |
| 4,959,948 | 10/1990 | Fleissner | 53/528 |

FOREIGN PATENT DOCUMENTS

| | | |
|---|---|---|
| 0210570 | 2/1987 | European Pat. Off. . |
| 0399564 | 5/1990 | European Pat. Off. . |
| 0462620 | 11/1990 | European Pat. Off. . |
| WO880258 | 12/1991 | PCT Int'l Appl. . |

OTHER PUBLICATIONS

U.S. Ser. No. 07/607,265, date Oct. 31, 1990, Bolstad.
U.S. Ser. No. 07/607,268, date Oct. 31, 1990, Bowns.

Primary Examiner—James J. Bell
Attorney, Agent, or Firm—Klarquist, Sparkman, Campbell, Leigh & Whinston

[57] ABSTRACT

A method is disclosed for the densification of crosslinked fibers having a crosslinking agent loading level of from about 2.5 molar to about 5 molar %. The crosslinked fibers are compressed from an initial density of from about 0.02 g/cc to about 0.04 g/cc to a second density of from about 0.20 g/cc to about 1.00 g/cc by either the simultaneous or sequential application of heat and pressure. The surface temperature of the press is typically between about 60° C. to about 180° C. The compression force for the air laid or wet laid webs is in the range of about 800 psi to about 115,000 psi. Densifying the crosslinked fiber in this manner produces a compressed web having enhanced absorbent capacities of from about 21 g/g to about 15 g/g.

30 Claims, 3 Drawing Sheets

METHOD OF DENSIFYING CROSSLINKED FIBERS

FIELD OF THE INVENTION

This invention relates to the formation of freestanding, densified absorbent structures from crosslinked high-bulk fiber.

BACKGROUND OF THE INVENTION

Crosslinked cellulose fiber has excellent absorbent properties and therefore has been used in the manufacture of products such as diapers and absorbent towels. Often, the fibers undergo crosslinking at a site remote from the product manufacturer's location. It is therefore common to transport the crosslinked fiber from its production site to the manufacturer's location. However, due to their bulk, transportation of such fibers can be costly.

Also, if such fibers are transported in bags or bales, they tend to form clumps during transport. An example of baling high-bulk fiber for transport is set forth in U.S. patent application Ser. No. 07/607,265, entitled "Method for Packaging and Shipping Fiber Material" filed Oct. 31, 1990, now U.S. Pat. No. 5,174,198. This case discloses restraining bales of crosslinked fibers by wires to prevent the fibers from expanding during transportation. One drawback of this approach is that refiberation equipment is typically required at the product manufacturer's facility to break up the agglomerated fibers prior to air laying or otherwise incorporating them into products.

For applications as absorbent products, it is desirable that compressed fibers retain their absorbency once the compression force is released. Balancing the need to compress the crosslinked fibers to facilitate transportation while maintaining the absorbency and springback of the fibers has proven difficult and costly.

Consideration has also been given to forming crosslinked fibers into undensified web structures and then transporting the preformed undensified webs, as in rolls, to the product manufacturer's facility. This eliminates the need to refiberize the webs if the webs are incorporated directly into a product, such as the core of a diaper. However, in undensified web format the webs are still bulky and the products made from such webs can also be bulky.

Attempts have also been made to compress webs of crosslinked fibers prior to shipment. However, because of the resilience of such fibers, they tend to spring back to their original bulk prior to shipment or prior to incorporation into a manufacturer's product. If enough force is applied to prevent springback, such as by using a hydraulic press, the fibers can be crushed with the absorbent capacity of the webs consequently being severely hampered.

U.S. Pat. No. 4,822,453 recognizes the difficulty of forming densified sheets of crosslinked fibers. One reason for this difficulty is that the fibers substantially expand once the compression force is released. This reference discloses crosslinked fibers loaded with from 0.5 to 3.5 molar percent crosslinking agent. This references also indicates that compressed webs having densities of from 0.12 to 0.6 g/cc have been achieved using a hydraulic press without listing the loading of these webs. However, the absorbent capacities of the webs (measured as the wet densities) for webs compressed to densities of 0.12 to 0.4 g/cc was stated as 0.06 g/cc and 0.12 g/cc. However, a wet density of 0.12 g/cc corresponds to relatively little expansion upon wetting at a relatively low compressed density of 0.40 g/cc. This reference mentions the possibility of increasing the compressibility of the webs by reducing the loading level of crosslinking agent or by mixing crosslinking fibers with uncrosslinked fibers. However, the capacity of webs to absorb liquid is believed to be hampered by reducing the amount of crosslinking agent used or by mixing a blend of crosslinked and uncrosslinked fibers.

Finally, it is known to compress wood pulp under heat and pressure, e.g. in paper making processes. However, compressed wood pulp absorbs relatively little liquid following compression and subsequent rewetting in comparison to the absorbent capacity of the crosslinked fibers.

Therefore, a need exists for improved densified webs of crosslinked fibers and an improved method of making such webs.

Accordingly, a first object of the present invention is to provide an improved method of compressing crosslinked high-bulk fibers into densified absorbent structures.

A second object of the present invention is to provide an improved method of compressing crosslinked fibers which is versatile and which does not cause structural damage to the fibers upon application of the compression force.

A third object of the present invention is to provide highly densified absorbent structures of high-bulk crosslinked fibers which retain their shape upon release of the compression force and yet maintain an excellent absorbent capacity upon wetting.

SUMMARY OF THE INVENTION

Densified freestanding absorbent structures of high-bulk crosslinked fibers are formed by the simultaneous application of heat and pressure to the fibers. The compressed high-bulk fiber structure or web not only retains its densified nature and lower bulk once the compression force is released, but also, upon wetting, expands and substantially retains its capacity to absorb fluids relative to undensified webs.

The method of the present invention comprises preparing the crosslinked high-bulk fiber using conventional methods, Once the crosslinked fiber has been prepared, it is thereafter layered into mats having a first density, such as from about 0.02 g/cc to about 0.04 g/cc with a typical density of approximately 0.03 g/cc. The fiber may be air laid or wet laid in a conventional manner into a web. Air laid webs are typically easier to compress under heat and pressure to the desired density; however, it has been discovered that the capacity of such webs to absorb liquid is slightly less than if the web is initially wet laid. Once the high-bulk fiber has been laid into mats it is then heated and compressed to the desired density.

A preferred embodiment of the present invention involves hot pressing the crosslinked fiber web using either a heated platen press or heated calendar rolls. The material is densified by applying a compression force wherein the surface temperature of the press or calendar rolls is typically from about 60° C. to about 180° C. However, the upper temperature range is preferably maintained below the scorch temperature of the fibers, which is about 175° C. for cellulose. Above such temperatures, the cellulose tends to discolor or scorch.

A compression force is applied to the fibers in the range of from about 800 psi to about 115,000 psi, with the most preferred range being from about 2,000 psi to about 4,000 psi. The application of heat and pressure in this manner forms freestanding absorbent web structures of high-bulk fiber having compressed densities of from about 0.20 g/cc (for 800 psi pressure) to about 1.00 g/cc (for 115,000 psi pressure). The webs compressed to second densities of 0.20 g/cc to 1.00 g/cc have respective pad absorbency capacities of from about 21 g/g to about 17 g/g. These crosslinked fiber structures have a combination of density and absorbency characteristics not known in the prior art.

Air laid high-bulk fiber (or wet laid fiber) may contain a crosslinking catalyst, such as acidic salts. Crosslinking catalysts are useful for accelerating the crosslinking reaction when urea-based crosslinking substances are used. When catalysts are used, the required compression temperature is lower than is required for web without the catalysts. When air laid web containing a crosslinking agent catalyst is compressed, the press surface temperature may range from about 60° C. to about 100° C. with a typical temperature of about 65° C. Compression temperatures may be slightly higher for wet laid web.

Although pressing the fibers with a press surface heated to the requisite temperature is a preferred embodiment of the present invention, the high-bulk fiber web can be preheated and then delivered to a press as long as sufficient heat is retained by the fibers to enable subsequent compression at the desired temperatures. The fibers can be heated in conventional manners known in the art, including, but not limited to, steam heating the fibers. The preheating web approach is particularly useful when crosslinking agent catalysts are included in the web.

The webs may further contain super absorbent polymers. These polymers enhance the absorbency of the webs and thus facilitate subsequent applications of the web as absorbent products.

These and other objects, features and advantages of the present invention will become apparent with reference to the following description and drawings.

DETAILED DESCRIPTION

Figure 1:
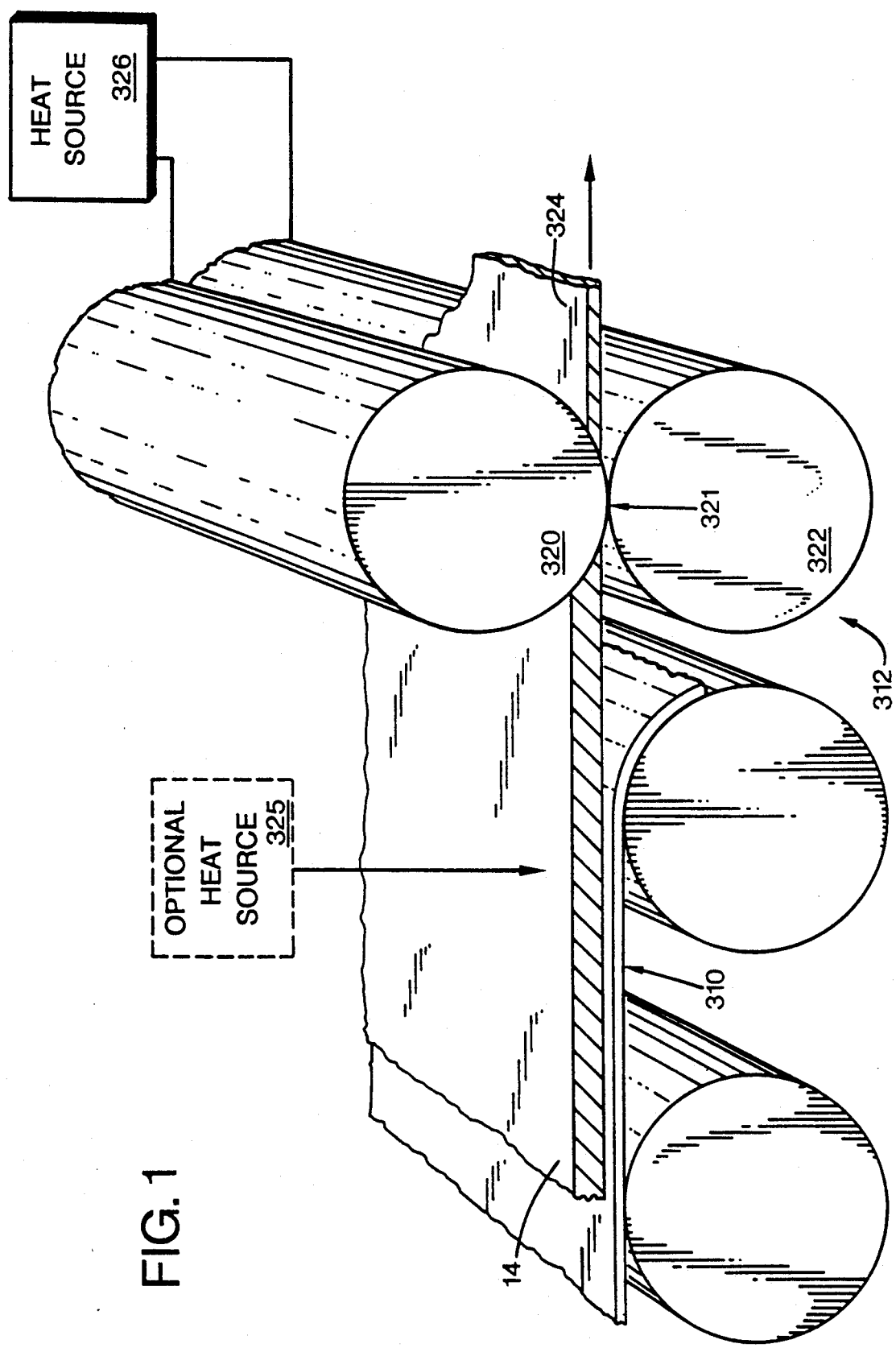
FIG. 1 is a schematic side elevational view of a calendar roll press in the process of hot pressing a web of high-bulk crosslinked fibers.
Figure 2:
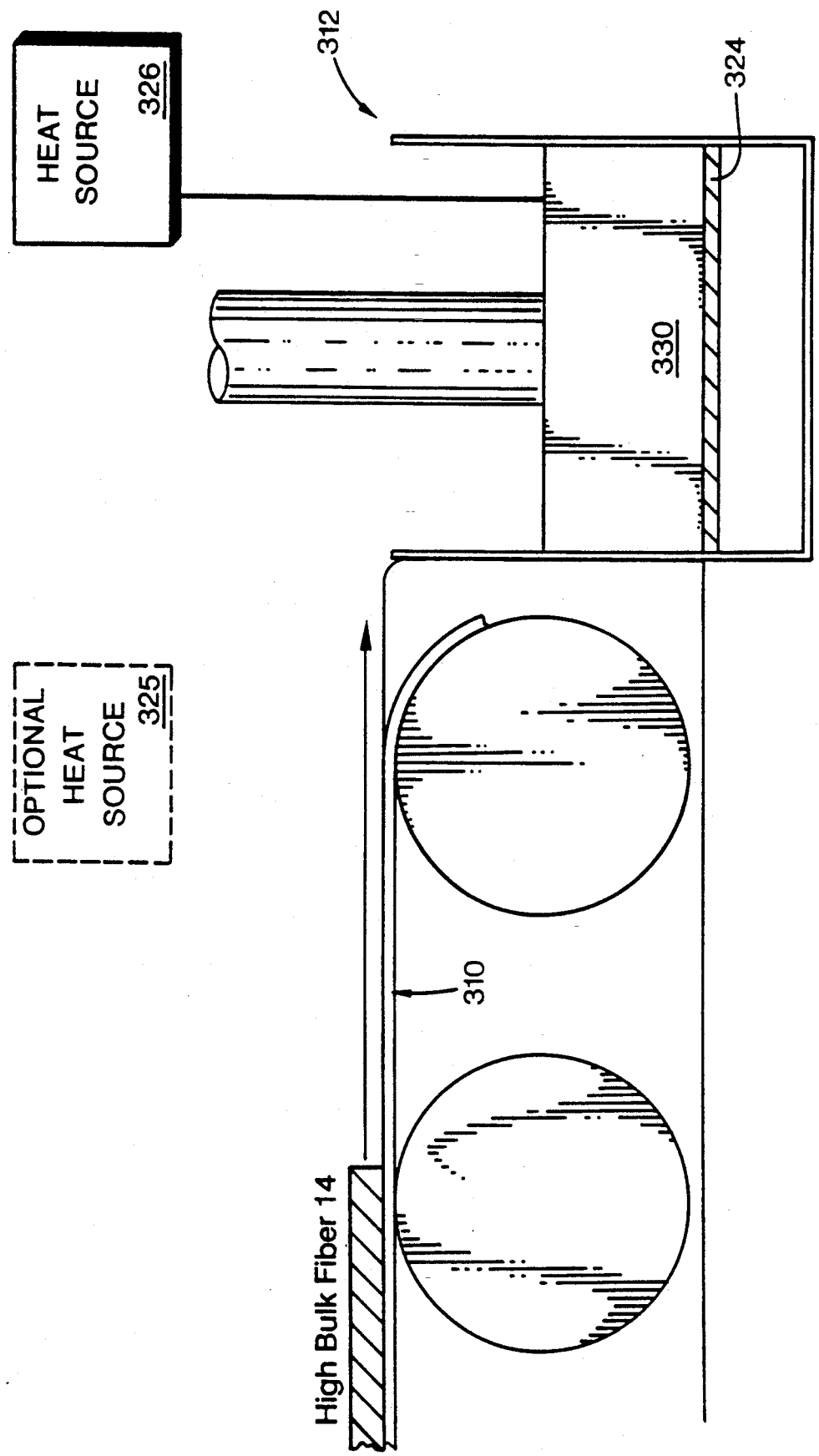
FIG. 2 is a schematic oblique view of a platen press in the process of hot pressing a web of high-bulk crosslinked fibers.

With reference to FIG. 1, crosslinked high-bulk fiber in the form of an air laid or wet laid web or mat 14 is transported along conveyer 310 to a hot press 312. Although any hot press capable of generating the desired heat and pressure may be used, the FIG. 1 form of press comprises a pair of calendar rolls 320, 322 which define a nip 321 therebetween through which the web 14 is continuously fed to produce a densified web 324 at the outlet of the nip. A heat source 326 provides heat to the calendar rolls 320, 322 as described below. In FIG. 2, the hot press 312 is illustrated as a conventional platen press 330 coupled to the heat source 326. In connection with FIG. 2, the fibers may simply be directly laid into the press or delivered to the press in the form of web section or mats 14.

Heat source 326 is capable of heating calendar rolls 320 and 322 (FIG. 1) to a surface temperature of at least about 140° C. to about 180° C. The surface temperature of the calendar rolls is regulated to prevent damage to the fibers. It has been found that temperatures greater than about 175° C. begin to cause damage to the fibers as evidenced by yellowing or scorching of the fibers.

The crosslinked high-bulk fiber may be formed in a conventional manner. One specific example of a method used in the formation of the high-bulk fibers is disclosed below. Although variable, the high-bulk fiber web 14, either air laid or wet laid, has a typical initial density of from about 0.02 g/cc to about 0.04 g/cc, with about 0.03 g/cc being one common initial or first density.

To facilitate transportation of the crosslinked high-bulk fiber to the manufacturer's production site the crosslinked fiber is compressed from an initial first density and a first volume to a compressed second density and second volume by the simultaneous application of heat and pressure. The resulting compressed web or mat is a non-woven sheetlike structure comprising cellulose fibers or other fibers that are covalently bonded together.

Cold pressing high-bulk crosslinked fiber is not satisfactory. For example, compressing the volume of high-bulk crosslinked fiber from a first density of 0.031 g/cc to a second density of 0.17 g/cc with this second density being retained following removal of the compression force and, wherein the crosslinking agent is employed in an amount of about 2.5% to about 5.0% (the "loading level") has required a compression force of about 28,000 psi. A second density of only 0.17 g/cc does not represent a meaningful densification of the high-bulk fiber as the web is still of relatively high-bulk for transportation purposes. Eventually, as the pressure is increased to the point where significant densification occurs, the fibers are damaged by the excessive pressure. This reduces the liquid absorbency capacity of the densified material.

Maintaining the fiber in a densified state is important for the transportation of the fibers. However, even more important for subsequent absorbent product applications is the requirement that the fibers retain substantial absorbent capacity in the densified state.

The absorbent capacity of the compressed fibers can be quantified either as the pad capacity or as the wet density. The pad capacity is defined as the number of grams of fluid absorbed by the compressed mats 324 per gram of fiber in the mat. The wet density is defined as the density of the crosslinked fibers once the compressed fibers at the second density are treated with fluid using a process for determining the saturation point as described below. The relationship between the pad capacity and the wet density is approximately reciprocal in nature. That is, the reciprocal of the wet density is approximately equal to the pad capacity.

As a general matter, the greater the loading level, the greater the absorbent capacity of the densified fibers and the more difficult the fibers are to densify. However, it has surprisingly been found that when both heat and pressure are applied to a web or mat of crosslinked fibers having loading levels between about 3.5 molar % to about 5.0 molar %, the web remains in a densified state following removal of the compression force. Further, the pad capacities are in the range of about 21 g/g (when densified to about 0.25 g/cc) to about 17 g/g (when densified to about 1.0 g/cc) depending upon the pressure applied to the pad and the resulting density (see Example 1).

For purposes of comparison, fiber webs 14 produced as described in connection with FIG. 3 below and having an initial density of about 0.031 g/cc, and a crosslinking loading level of about 3.8 molar %, have been found to have a typical pad capacity of about 24 g/g to about 26 g/g prior to compression to the second density. A pad compressed according to the present invention having a capacity of 21 g/g represents over 80% of a 26 g/g initial capacity while a compressed pad having a capacity of 17 g/g represents over 65% of a 26 g/g initial capacity. Therefore, the compressed pads of the present invention retain a substantial majority of the initial pad capacity even when densified so as to make them easier to transport.

A method of determining the absorbent capacity involves positioning a compressed mat section (typically a 4"×4" section) on a platform inclined at about 5°. Liquid, such as synthetic urine, is applied to the center of the compressed mat at a flow rate of about 5 mls/s. The flow of liquid is continued until the mat is saturated, that is until the first evidence of flow from the mat down the incline is visually detected. The pad absorbent capacity is then equal to the liquid retained by the mat in grams relative to the weight of fiber in the mat in grams.

The pad capacity, the compressed density of the fibers, and the compression force applied to achieve the compressed density for wet laid webs 14 are shown in example 1 below. For wet laid webs, the data indicates that the compression force can range anywhere from about 800 to 115,000 psi with excellent pad absorbent capacity still being maintained upon wetting. A significant densification of the high-bulk fibers is illustrated by the data in example 1. At 800 psi, the fibers are compressed from an initial density of 0.025 g/cc to a compressed density of 0.25 g/cc. The compressed fibers at a second density of 0.25 g/cc have a pad capacity of 20.7 g/g. At 28,800 psi, the web density is 0.85 g/cc, while the pad capacity is 17.7 g/g. Thus, the data in example 1 indicates that a rather high level of densification can be achieved by hot pressing the fibers while maintaining the pad capacity of the high bulk fibers.

A preferred embodiment of the present invention utilizes wet laid fibers having a crosslinking material added to about 2.5 molar percent to about 5.0 molar percent, with a preferred loading level of about 3.8 molar percent. Wet laid webs 14 are then transported to calendar press 312 having press rolls 320, 322 heated to a surface temperature of about 170 degrees C. The fiber webs 14 are then compressed to a second density of about 0.30 to about 0.40 g/cc by applying a compression force of about 2000 psi to about 4000 psi. Compressed fiber mats 324 formed in this manner have a pad capacity of about 20 g/g to about 19 g/g. This represents about 70% or more (19/26≈70%) of the undensified capacity of the pads.

As can be seen from example 2 below, a significant densification of high-bulk fiber webs 14 also results from hot pressing air laid webs. High-bulk fiber webs 14, having been air laid at an initial density of from about 0.02 g/cc to about 0.04 g/cc and more typically 0.03 g/cc are compressed in a similar manner as described for the compression of wet laid fiber in the foregoing paragraphs. The temperatures may also be the same.

However, air laid high-bulk fiber (or wet laid fiber) may contain a crosslinking catalyst, such as acidic salts. Crosslinking catalysts are useful for accelerating the crosslinking reaction when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used. When catalysts are used, the surface temperature required of the calendar rollers 320 and 322 or platen press 330 is lower than is required for web without the catalysts. Thus, typical press surface temperatures are about 100° C. for a catalyst including crosslinked fiber, as compared to 170° C. for a non-catalyst including crosslinked fibers. When air laid web 14 containing crosslinking agent catalyst is compressed, the press surface temperature may range from about 60° C. to about 170° C. with a typical temperature being about 95° C.

Pressing the fibers with a press surface heated to the requisite temperature is a preferred embodiment of the present invention because preheating fibers can cause the fibers to become brittle and damaged during pressing. However, the high-bulk fiber web 14 can be preheated and then delivered to a press as long as sufficient heat is retained by the fibers to enable subsequent compression at the desired temperatures and that temperatures are low enough to avoid brittleness of the fibers. The fibers can be heated in conventional manners known in the art, including, but not limited to, steam heating the fibers. Typical preheat fiber temperatures would be from about 60° C. to about 140° C. With reference to FIGS. 1 and 2, optional heating source 325 can be provided to heat fiber web 14 prior to applying the compression force with calendar rolls 320, 322 or platen press 312.

Preheating fiber web 14 is particularly applicable when crosslinking agent catalysts are included in web 14 because the fibers can be kept at a lower temperature and still be densified as compared to cases wherein a catalyst is not used. However, it will be recognized by those skilled in the art that preheating web 14 is also useful for webs which do not include catalysts as long as the webs can retain sufficient heat due to preheating to facilitate densification during the compression phase.

Without being limited to a particular theory of operation, it is believed that hot pressing causes crosslinking between individual fibers and allows the densification of the web structures. Thus, the temperature is preferably at the level to facilitate this action and would vary with the particular crosslinking agents and catalysts, if used.

As an alternative to compressing web 14 to a second density which is then ready for use in absorbent products, web 14 may be compressed to a second density and then "tenderize" by the use of a mechanism which mechanically breaks up some of the bonds in the web. The web still remains substantially bonded, however. As one example, the webs may be passed through the nips of cross machine direction and machine direction corrugators to reduce their stiffness. The stiffness may be controlled by adjusting the clearance between the nips. Although not limited to a specific approach, examples of suitable corrugators and tenderizing procedures are disclosed in U.S. Pat. Nos. 4,559,050, 4,596,567 and 4,605,402. The resulting material can be used in a conventional manner to manufacture a wide variety of products, such as absorbent pads and diapers.

The high-bulk fiber web 14 may further include super absorbent polymers. These polymers are known in the art and enhance the absorbency of the webs and thus facilitate subsequent applications of the web as absorbent products. These polymers may simply be mixed with the fibers in the web and may be in place, as by adhesive or in pockets formed in the web.

Example 2 below indicates that air laid fibers can be compressed to densities of at least about 0.85 g/cc and yet still exhibit pad capacities which are appropriate for absorbent product applications. However, comparing the pad capacities in example 1 with example 2 indicates that the pad capacities for air laid compressed fibers are somewhat less than the pad capacities for wet laid fibers. Nevertheless, both air laid webs and wet laid webs having loading levels of about 2.5 molar % to about 5.0 molar %, when heat pressed show significantly increased pad capacities and retain a substantial majority of their initial uncompressed pad capacity.

EXAMPLE 1

Example 1 refers to the densification of wet laid high-bulk crosslinked fiber from an initial density of about 0.025 g/cc. The crosslinked fibers were made as explained below in connection with FIG. 3, and were slurred and wet laid in a conventional manner. The fibers contain about 3.8 molar % crosslinking agent (specifically, dimethyloldihydroxyethylene urea). These fibers were compressed by a platen at a press surface temperature of about 140° to about 180° C., and more specifically at about 170° C.

TABLE 1

WET LAID DENSIFIED HBA
EFFECT OF PRESS PRESSURE ON
PAD DENSITY AND PAD CAPACITY

| Pressure, psi | Density g/cc | Wet Density g/cc | Pad Capacity g/g |
|---|---|---|---|
| 800 | .25 | .048 | 20.7 |
| 3,200 | .36 | .052 | 19.4 |
| 6,400 | .49 | .055 | 18.1 |
| 12,800 | .65 | .055 | 18.2 |
| 14,400 | .79 | .056 | 17.9 |
| 28,800 | .85 | .056 | 17.7 |

EXAMPLE 2

Example 2 illustrates the compression and densification of air laid fiber from an initial density of about 0.025 g/cc using a hydraulic platen press to achieve the second density. The surface temperature of the platen press was about 96° C. The fibers were crosslinked as described below in connection with FIG. 3. The level of crosslinking agent (dimethyloldihydroxyethylene urea) added was approximately 3.8 molar % and the catalyst used was about an 80:20 mixture of aluminum chloride and magnesium chloride, the mixture being added at about 0.70 molar %.

TABLE 2

AIR LAID DENSIFIED HBA

| Pressure, psi | Density g/cc | Pad Capacity g/g |
|---|---|---|
| 180 | 0.08 | 19.1 |
| 2,700 | 0.20 | 17.3 |
| 9,000 | 0.40 | 15.2 |
| 14,400 | 0.60 | 15.2 |

EXAMPLE 3

Example 3 illustrates, as a control, the densification of air laid wood pulp available as NB 316 wood pulp from Weyerhaeuser Company of Tacoma, Wash. The wood pulp does not have crosslinking agent added to the fibers. NB 316 was hot pressed in a platen press at a temperature of 96° C.

TABLE 3

DENSIFIED NB 316

| Pressure, psi | Density g/cc | Pad Capacity g/g |
|---|---|---|
| 36 | 0.08 | 16.0 |
| 143 | 0.20 | 12.2 |
| 340 | 0.40 | 7.7 |
| 1,290 | 0.60 | 5.2 |

Thus, as wood pulp is densified under heat and pressure, its pad capacity is substantially degraded.

MANUFACTURE OF CROSSLINKED FIBERS

The crosslinked high-bulk fiber webs 14 can be formed in a number of ways, one specific example of which is described hereinafter. In particular, this approach is set forth in co-pending U.S. patent application, Ser. No. 07/607,268, entitled "Fiber Treatment Apparatus", now abandoned, which is incorporated herein by reference.

Figure 3:
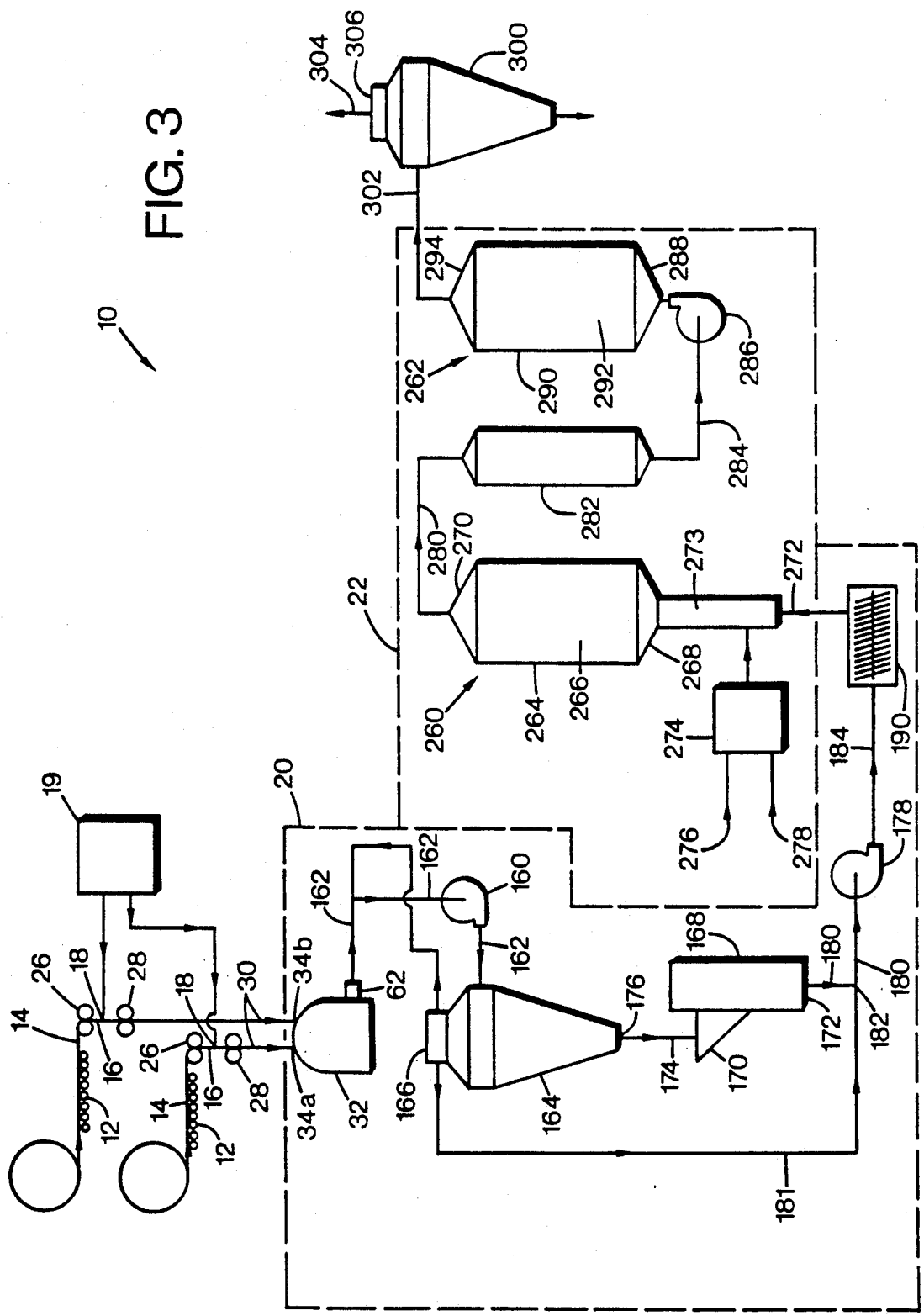
FIG. 3 is a schematic depiction of the components of an apparatus used in producing high-bulk fibers.

The schematic representation of the apparatus used to form the fibers is shown in FIG. 3. The apparatus depicted in FIG. 3 comprises the following components: a conveying device 12 for transporting a web 14 of cellulose fibers or other fibers through a fiber treatment zone 16; an applicator 18 for applying a treatment substance such as a crosslinking substance from a source 19 thereof to the web 14 at the fiber treatment zone 16; fiberizer 20 for completely separating the individual cellulose fibers comprising the web 14 to form a fiber output comprised of substantially unbroken cellulose fibers; and a dryer 22 coupled to the fiberizer for flash-evaporating residual moisture from the fiber output and for curing the crosslinking substance, thereby forming dried and cured cellulose fibers.

The fibers used in the present invention may be obtained from wood pulp or other sources. A de-bonding agent is typically applied to the web either after the formation of the web or prior thereto although it is not necessary to add such de-bonding agents to the fibers. The de-bonding agent can be added by using any conventional paper making machinery. De-bonding agents tend to minimize interfiber bonds between fibers of the web. Suitable de-bonding agents include, but are not limited to, Berocell 584 from Berol Chemicals, Incorporated of Metairie, La. in a 0.025% weight of de-bonder to weight of fiber.

Crosslinked cellulose fibers are individual fibers each comprised of multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents". Suitable crosslinking agents are generally of the bifunctional type which create covalently bonded "bridges" between said neighboring hydroxyl groups.

Crosslinked cellulose fibers have particular applicability not only in wrinkle-resistant fabrics but also in materials derived from wood pulp having one or more desirable characteristics such as high loft, low density, high water absorbency, resiliency, and light weight. As a result, crosslinked cellulose fibers are candidates for use in absorbent structures found in disposable products such as diapers and pads. They are also useful for paper toweling, wiping cloths, filters, and other similar uses.

Cellulose fibers in the web 14 should be in a nonwoven configuration produced by a pulping process or the like, such as in a paper mill, and can be bleached or unbleached. The web 14 can have any of a wide variety of basis weights. It is normally not necessary that cellulose fibers comprising web 14 be completely dry. Since cellulose is a hydrophilic substance, molecules thereof will typically have a certain level of residual moisture, even after air drying. The level of residual moisture is generally 10% w/w or less, which is not detectable as "wetness".

Conveying device 12, which may comprise a conveyor belt for example, carries the mats through the fiber treatment zone 16. At the fiber treatment zone 16, sprayers or other applicators 18 apply crosslinking agents to the web 14. Chemicals are typically applied uniformly to both sides of the web. The wetted web passes between a first pair of rollers 26 and a second pair of rollers 28 which assist in distributing the chemicals uniformly through the mat. Other applicators may also, of course, be used.

The crosslinking substance is a liquid solution of any of a variety of crosslinking solutes known in the art. If required, the crosslinking substance can include a catalyst to accelerate the bonding reactions between molecules of the crosslinking substance and cellulose molecules. However, many, if not most, crosslinking substances do not require a catalyst.

Preferred types of crosslinking substances are selected from a group consisting of urea derivatives such as methylolated urea, methylolated cyclic ureas, methylolated lower alkyl substituted cyclic ureas, methylolated dihydroxy cyclic ureas, and mixtures thereof. A specifically preferred crosslinking substance would be dimethyloldihydroxyethylene urea (DMDHEU). In addition, crosslinking substances can be based on polycarboxylic acids. Other crosslinking materials are known in the art, such as described in U.S. Pat. No. 3,440,135 to Chung, U.S. Pat. No. 4,935,022 to Lash, et al., U.S. Pat. No. 4,889,595 to Herron, et al., U.S. Pat. No. 3,819,470 to Shaw, et al., U.S. Pat. No. 3,658,613 to Steijer, et al., U.S. Pat. No. 4,822,453 to Dean et al. and U.S. Pat. No. 4,853,086 to Graef, et al., all of which are hereby incorporated herein by reference.

Suitable catalysts include, for example, acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used.

Each web 14 is urged by the first and second pair of rollers 26, 28 through the fiber treatment zone 16 where the web is impregnated with a liquid crosslinking substance. The crosslinking substance is preferably applied to one or both surfaces of the web using any of a variety of methods known in the art useful for such a purpose such as spraying, rolling, dipping, or analogous method. Spraying has the advantage of consistent and rapid full coverage of a planar surface such as that of a mat at a controllable rate, especially when the spray is applied to a surface moving past a spray nozzle or analogous applicator at a fixed rate. Roller applicators have also proven to be reliable and effective in such applications as paper coating and the like and would therefore be effective for applying the crosslinking substance in the present instance. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

Once the fibers have been treated with crosslinking agent, the fibers go to the fiberizer 20 which serves to comminute one or more mats impregnated with the crosslinking substance into individual, substantially unbroken cellulose fibers comprising a fiber output. The fiberizer 20 performs its task on one or more mats, which are preferably still moist (but which may be dry) from application of the crosslinking agent. In this case, the wet sheets are delivered directly and immediately to the fiberizer by the conveyor 12 without aging or other significant delays. The preferred embodiment of the fiberizer 20 is an attrition device 32. The attrition device 32 preferably can simultaneously fiberize a plurality of impregnated mats and has a separate mat inlet 34a, 34b for receiving each corresponding impregnated mat. A first conveyor fan 160 of conventional design may be utilized for propelling the fibers from the outlet 62 of the attrition device 32 through a conduit 162.

An optional component of the fiberizer 20 is a first cyclone 164 or similar apparatus known in the art, utilized in a conventional manner to concentrate the fibers passing out of the outlet 62 of the attrition device 32. The first cyclone 164 receives the fibers through the conduit 162 coupled thereto.

Excess air may be recovered at the top 166 of the first cyclone 164 and recycled as required through a conduit 168 to a location upstream of the first conveyor fan 160. Such additional air may be beneficial for easing the transfer of the fibers through the first conveyor fan 160.

A disk refiner 168 is another optional component of the fiberizer 20 which may be employed to effect additional separation of fibers if required. The disk refiner 168 is of a type known in the art and comprises a disk refiner inlet 170 and a disk refiner outlet 172. If the disk refiner 168 is used, the inlet 170 thereof is coupled via a conduit 174 to an outlet 176 of the cyclone 164.

A second conveyor fan 178 may optionally be utilized to urge propagation of the fibers through a conduit 180 downstream of the disk refiner 168. Excess air may be recovered from the top 166 of the first cyclone 164 and routed via a conduit 181 to a tee 182 just upstream of its second conveyor fan 178.

Another optional component of the fiberizer 20 is a fluff generator 190 which receives the fibers from the optional second conveyor fan 178 through a conduit 184. Fluff generator 190 is effective for providing additional comminution, if required, of the fibers, particularly of residual knots in the comminuted fibers produced by the attrition device.

The dryer 22 receives the fiber output (at 272) from fiberizer 20, removes residual moisture from the fibers and cure the crosslinking agent. The dryer 22 may comprise a drying zone 273 for receiving fibers, e.g. from fluff generator outlet 204 and for removing residual moisture from the fibers via a "flash drying" method and a second drying zone 262 for curing the crosslinking agent. In FIG. 3, the curing starts in zone 260 and continues through zone 262.

FIG. 3 shows that zone 273 is coupled to the fluff generator outlet by a conduit 272 and to a source 274 of heated air, typically produced by combustion of a supply of natural gas 276 and fresh air 278. The temperature of dryer 22's heated air is regulated to maintain the temperature of the drying zone 273 within a range of about 200 degrees C. to about 315 degrees C. As the fiber output passes into the drying zone 273, the wet fibers comprising the fiber output are substantially instantaneously exposed to the high temperature in this zone. Such rapid exposure to high temperature imparts a "flash drying" effect to the fibers, thereby causing rapid and thorough drying. Such "flash drying" also tends to separate, in a microscopically explosive manner, fibers that are touching one another, thereby ensuring thorough separation of the fibers. The passage of time through the drying zone 273 is preferably less than one second, which is deliberately kept short to avoid overheating and scorching the fibers, which become highly susceptible to scorching after the residual moisture has been driven therefrom.

FIG. 3 also shows that the first zone 260 is comprised of a first tower 264 comprised of a body portion 266, an inlet 268 and a first tower outlet 270. The dryer zone 273 is coupled via a conduit 272 to the outlet of the fluff generator 190. It is also possible to couple the dryer zone 273 directly to the outlet 62 of the attrition device 32 if neither the fluff generator 190 or the disk refiner 168 are included.

In FIG. 3, the first tower outlet 270 is shown preferably coupled via a conduit 280 to a down tube 282, which is coupled via a conduit 284 to a third conveyor fan 286 located at an inlet 288 of a second tower 290. Second tower 290 includes the inlet 288, a second tower body 292 and an outlet 294 serving as an outlet of the dryer 22.

Dried fibers are propelled through the inlet 288 of the second tower 290 via the third conveyor fan 286. As the fibers are lofted through the second tower body 292, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as to not scorch the fibers during curing. It should be noted that single stage dryers may also be used.

FIG. 3 also shows a cyclone 300 of conventional design coupled via a conduit 302 to the dryer outlet 294, serving to concentrate the fibers passing therethrough in preparation for collection. Excess air 304 is vented through the top 306 of the second cyclone 300. The resulting concentrated fibers may be collected using any of a number of collection devices known in the art.

The foregoing paragraphs have described the principles of the present invention and have illustrated several preferred embodiments of the invention. It will be apparent to those skilled in the art that the invention may be modified without departing from the principles hereinbefore described. We claim all modifications within the scope of the following claims.

We claim:

1. A method of forming densified absorbent web structures from crosslinked fiber, the method comprising:
    forming a web of high-bulk crosslinked fiber having an absorbent capacity wherein the loading level of the crosslinking agent is from about 2.5 molar % to about 5.0 molar %; and
    applying heat and pressure to the web to compress the web from a first density to a second density, the web remaining in a densified state following removal of the pressure and retaining a substantial majority of the absorbent capacity of the uncompressed web.

2. The method according to claim 1 wherein the applied heat is sufficient to promote an external fiber to fiber crosslinking reaction.

3. The method according to claim 1 wherein the compression force is applied with the crosslinked fibers heated to a temperature in the range of from about 60° C. to about 100° C.

4. The method according to claim 1 wherein the compression force is applied with the crosslinked fibers heated to a temperature of about 140° C. to 180° C.

5. The method according to claim 4 wherein the compression force is applied with the crosslinked fibers heated to about 170° C.

6. The method according to claim 1 wherein the compression force is in the range of about 800 psi to about 115,000 psi.

7. The method according to claim 1 wherein the web is compressed to a density of from about 0.20 g/cc to about 1.0 g/c and wherein the densified web has an absorbent capacity of from about 17 g/g to about 21 g/g and has a density following the application of liquid to the densified pad of from about 0.06 g/cc to about 0.04 g/cc.

8. The method according to claim 1 wherein the web is formed by wet laying the crosslinked fibers.

9. The method according to claim 1 wherein the web is formed by air laying the crosslinked fibers.

10. The method according to claim 1 wherein the first density of the high bulk crosslinked fiber is from about 0.02 to 0.04 g/cc.

11. The method according to claim 1 wherein the second density is in the range of from about 0.20 g/cc to about 1.00 g/cc.

12. The method according to claim 11 wherein the second density is in the range of from about 0.40 g/cc to about 1.00 g/cc.

13. The method according to claim 12 wherein the absorbency capacity of the compressed web at the second density is about 15–21 g/g.

14. The method according to claim 1 wherein the web is formed of crosslinked high-bulk fibers treated with a crosslinking agent selected from the group consisting of dimethyloldihydroxyethylene urea, methylolated urea, methylolated cyclic ureas, methylolated lower alkyl substituted cyclic ureas, methylolated dihydroxy cyclic ureas, and polycarboxylic acids.

15. The method according to claim 1 wherein the loading level of the crosslinking agent is about 3.8 molar %.

16. The method according to claim 1 wherein the web is treated with a crosslinking agent catalyst selected from the group consisting of ammonium chloride, ammonium sulfate, aluminum chloride, magnesium chloride and alkali metal salts of phosphorous-containing acids.

17. The method according to claim 1 wherein the web includes super absorbent polymers.

18. The method according to claim 1 wherein the step of applying pressure to the web involves passing the web of crosslinked fibers on a continuous basis through the nip of at least one pair of heated calendar rolls.

19. The method according to claim 1 wherein the step of applying pressure to the web involves pressing the web of crosslinked fibers with a heated platen press.

20. A method of forming densified absorbent web structures from crosslinked fiber, the method comprising:
forming a web of high-bulk crosslinked fiber having an absorbent capacity;
heating the web from a first temperature to a second temperature; and
applying pressure to the heated web to compress the web from a first density to a second density, the web remaining in a densified state following removal of the pressure and retaining a substantial majority of the absorbent capacity of the uncompressed web.

21. The method according to claim 20 wherein the applied heat is sufficient to promote a crosslinking reaction between the high-bulk fibers.

22. A method according to claim 20 wherein the web is heated to a temperature of about 60° C. to about 180° C.

23. The method according to claim 20 wherein the web is formed of crosslinked high-bulk fibers treated with a crosslinking agent selected from the group consisting of dimethyloldihydroxyethylene urea, methylolated urea, methylolated cyclic ureas, methylolated lower alkyl substituted cyclic ureas, methylolated dihydroxy cyclic ureas, and polycarboxylic acids.

24. A method according to claim 20 wherein the web is treated with a crosslinking agent catalyst selected from the group consisting of ammonium chloride, ammonium sulfate, aluminum chloride, magnesium chloride and alkali metal salts of phosphorous-containing acids.

25. A method according to claim 24 wherein the web is heated to a temperature of about 60° C. to about 100° C.

26. The method according to claim 20 wherein the loading level of the crosslinking agent is about 2.5 molar % to about 5 molar %.

27. The method according to claim 20 wherein the web includes super absorbent polymers.

28. The method according to claim 1 wherein the web is formed of crosslinked high-bulk fibers treated with a crosslinking agent catalyst selected from the group consisting of ammonium chloride, ammonium sulfate, aluminum chloride, magnesium chloride and alkali metal salts of phosphorous-containing acids.

29. A method of forming densified absorbent web structures from crosslinked fiber, the method comprising:
forming a web of high-bulk crosslinked fiber having an absorbent capacity; and
applying heat and pressure to the web to compress the web from a first density of about 0.40 g/cc to a second density of about 1.00 g/cc, the web remaining in a densified state following removal of the pressure and retaining a substantial majority of the absorbent capacity of the uncompressed web.

30. A method of forming densified absorbent web structures from crosslinked fiber, the method comprising:
forming a web of high-bulk crosslinked fiber having an absorbent capacity, wherein the loading level of the crosslinking agent is from about 2.5% to about 5.0%,; and
applying heat and pressure to the web to compress the web from a first density to a second density from about 0.40 g/cc to about 1.00 g/cc, the web remaining in a densified state following removal of the pressure and retaining a substantial majority of the absorbent capacity of the uncompressed web.

* * * * *